United States Patent [19]

Patrick

[11] Patent Number: 5,120,714
[45] Date of Patent: Jun. 9, 1992

[54] METHOD FOR THE DIAGNOSIS AND TREATMENT OF HUMAN GRANULOMATOUS INFLAMMATORY DISEASE

[75] Inventor: Herbert Patrick, Philadelphia, Pa.
[73] Assignee: Thomas Jefferson University, Philadelphia, Pa.
[21] Appl. No.: 599,677
[22] Filed: Oct. 17, 1990
[51] Int. Cl.⁵ .................. A61K 39/395; A61K 37/04; A61K 49/00
[52] U.S. Cl. ........................ 514/21; 514/12; 424/85.8; 436/63
[58] Field of Search .............. 436/63; 514/12, 21; 424/85.8

[56] References Cited

PUBLICATIONS

Patrick et al., Am Rev Respir Dis 141 (4 part 2) 1990 A796.
Patrick et al., Am Rev. Respir. Dis 139 (4 part 2) 1989, A455.
Turk, J. L. et al., "The mononuclear phagocyte system in granulomas", Brit. J. Derm. 1985; 113:49–54.
Takizawa et al., "Granulomatous pneumonitis induced by Bacille Calmette-Guerin in the mouse and its treatment with cyclosporin", 1986; 134:296–299.
Chang et al., "Histology of granulomatous inflammation in nude rats lungs induced by complete Freund's Adjuvant (CFA)", Grassi et al.: Sarcoidosis and other Granulomatous Disorders, Amsterdam: Excerpta Medica; 1988, pp. 717–718).
Carrick and Boros, "The artificial granuloma 1: in vitro lumphokine production by pulmonary artificial hypersensitivity granulomas", Clin Immun and Immunopath, 1980: 17:415–426.
Horowitz et al., "Angiotensin converting enzyme concentrations in rabbit with talc-induced pulmonary granulomatosis", Am Rev Resp Dis, 1981; 124:306–309.
Remick et al., "Flow-cytometric evaluation of lymphocyte subpopulations in synchronously developing Schistosoma mansoni egg and sephadex bed pulmonary granulomas", Am J Path, 1988; 131:298–307.
Newman, "Antigen-specific T-cells in a mouse model of beryllium disease", Grassi C., Rizzato G. Pozzi E., eds.: Sarcoidosis and Other Granulomatous Disorders, Amsterdam: Excerpta Medica; 1988, pp. 715–716.
Kasahara et al., "Direct evidence for granuloma-inducing activity of interleukin-1: induction of experiental pulmonary granuloma formation in mice by interleukin-1-coupled beads", Am J Path, 1988, 130:629–637.
Boros, D. l., "Immunoregulation of granuloma formation in murine Schistosomiasis mansoni", Ann NY Acad Sci, 1986; 465:313–323.
deBrito et al., "Host granulomatous response in Schistosoma mansoni-antibody and cell-mediated damage of parasite eggs in vitro", J Clin Invest, 1984; 74:1715–1723.
Doughty et al., "Delayed type hypersensitivity granuloma formation around Schistosoma mansoni eggs in vitro", Am J Trop Med Hyg 1984; 33:1173–1177.
Ohta et al., "Schistosoma japonicum egg antigen-specific T-cell lines in man–induction of helper and suppressor T-cell lines and clones in vitro in a patient with chronic Schistosoma japonica", J Clin Invest, 1988; 775–781.
Bentley et al., "In vitro delayed hypersensitivity granuloma formation-development of an antigen-coated bead model", J Immunol, 1985; 134:4163–4169.
Mishra et al. "In-vitro sarcoid granulomas—differences between active and inactive disease", Grassi et al.: Sarcoidosis and Other Granulomatous Disorders, Amsterdam: Excerpta Medica; 1988, pp. 151–154.
Maguire, G. A., et al., "A continuous monitoring spectrophotometric method for the measurement of angiotensin converting enzyme in human serum", Ann Clin Biochem, 1985; 22:204–210.

Primary Examiner—Howard E. Schain
Assistant Examiner—Choon Koh
Attorney, Agent, or Firm—Woodcock Washburn Kurtz Mackiewicz & Norris

[57] ABSTRACT

A method for the diagnosis of human granulomatous inflammatory disease comprising determining the level of Granuloma Enhancing Factor (GEF) activity in a bodily fluid and comparing said level to established diagnostic levels is provided. Methods for treatment of human granulomatous diseases are also provided.

8 Claims, 1 Drawing Sheet

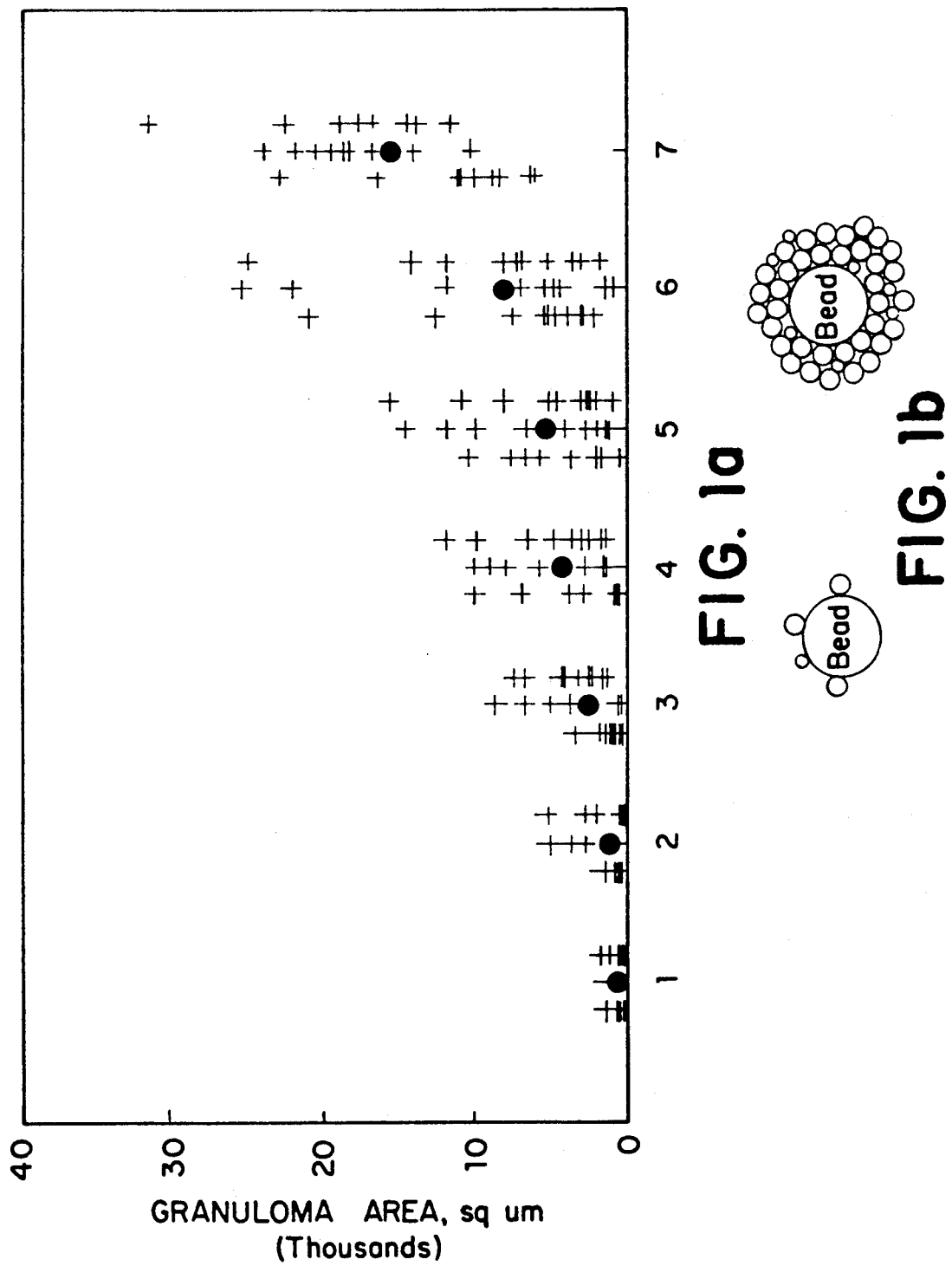

METHOD FOR THE DIAGNOSIS AND TREATMENT OF HUMAN GRANULOMATOUS INFLAMMATORY DISEASE

BACKGROUND OF THE INVENTION

Granulomas have traditionally been classified into two categories, non-immunologic (foreign body) and immunologic (hypersensitivity), although there may be overlap.

Human granulomatrous inflammation occurs against known antigens such as mycobacteria, fungi, parasites, and foreign particles such as talc and beryllium. These antigens are not capable of being phagocytized and cleared by polymorphonuclear cells. However, in human granulomatous diseases such as sarcoidosis, Wegener's granulomatosis, primary biliary cirrhosis and Crohn's disease, no inciting antigen has been identified and the idiopathic granulomatous inflammation can be physiologically detrimental. There have been no satisfactory experimental models for the study of human granulomatous inflammation and hence many questions remain unanswered concerning the immunology, regulation of granulomas and appropriate clinical treatment Investigations of the mechanisms regulating human granulomatous inflammation have been limited by the lack of suitable animal and in vitro models. The earliest bead model of granulomatous inflammation was the mouse pouch assay where polyacrylamide beads were injected into a subcutaneous air filled skin pouch. The resulting cellular infiltrates in the pouch were predominantly mononuclear cells forming granulomata. Subsequently, immunologic reactions were successfully modeled in vitro using antigen coated polyacrylamide beads and peripheral blood mononuclear cells (PBMC). The PBMC, in the absence of autologous sera, react to polyacrylamide beads coated with the proper antigen, reflecting the immune status of the host.

Non-immunologic, foreign body granulomas have been studied in guinea pigs (Turk, J.L. et al., "The mononuclear phagocyte system in granulomas", Brit. J. Derm. 1985; 113:49-54), mice (Takizawa et al., "Granulomatous pneumonitis induced by Bacille Calmette-Guerin in the mouse and its treatment with cyclosporin", 1986; 134:296-299) and athymic rats (Chang et al., "Histology of granulomatous inflammation in nude rats lungs induced by complete Freund's Adjuvant (CFA)" In: Grassi et al. Sarcoidosis and Other Granulomatous Disorders, Amsterdam: Excerpta Medica; 1988, pp. 717-718). Non-immunologic granulomas can also be produced by foreign body injection such as Sepharose-4B into mice (Carrick and Boros, "The artificial granuloma 1: in vitro lumphokine production by pulmonary artificial hypersensitivity granulomas", Clin Immun and Immunopath, 1980: 17:415-426), talc into rabbits (Horowitz et al., "Angiotensin converting enzyme concentrations in rabbit with talc-induced pulmonary, granulomatosis", Am Rev Resp Dis, 1981; 124:306-309) and Sephadex beads into mice (Remick et al., Flow-cytometric evaluation of lymphocyte subpopulations in synchroncusly developing schistosoma mansoni egg and sephadex bed pulmonary granulomas", Am J Path, 1988; 131:298-307). All of these animal models of non-immunologic granulomas provide little information concerning the mechanisms of human immunologic granulomatous inflammation.

Immunologic granulomas in animals have been recently produced by injections of beryllium in mice (Newman, "Antigen-specific T-cells in a mouse model of beryllium disease. In: Grassi C, Rizzato G. Pozzi E., eds.: Sarcoidosis and Other Granulomatous Disorders, Amsterdam: Excerpta Medica; 1988, pp. 715-716) and latex beads covered with interleukin-1 (Kasahara et al., "Direct evidence for granuloma-inducing activity of interleukin-1: induction of experimental pulmonary granuloma formation in mice by interleukin-1-coupled beads", Am J Path, 1988, 130:629-637) demonstrating that selected foreign materials may account for non-immunologic versus immunologic granuloma formation.

Immunologic granuloma formation and regulation has been extensively studied in schistosomiasis using animal and human PBMC exposed to schistosoma whole eggs to form in vitro granulomas (IVG's) (Boros, D.L., "Immunoregulation of granuloma formation in murine schistosomiasis mansoni", Ann NY Acad Sci, 1986; 465:313-323; de Brito et al., "Host granulomatous response in Schistosoma mansoni-antibody and cell-mediated damage of parasite eggs in vitro", J Clin Invest, 1984; 74:1715-1723; Doughty et al., "Delayed type hypersensitivity granuloma formation around Schistosoma mansoni eggs in vitro", Am J Trop Med Hyg 1984; 33:1173-1177; Ohta et al., "Schistosoma japonicum egg antigen-specific T-cell lines in man-induction of helper and suppressor T-cell lines and clones in vitro in a patient with chronic Schistosoma japonica", J Clin Invest, 1988; 81:775-781). These in vitro granuloma (IVG) models disclosed a cell-mediated response and were refined by substituting the whole schistosoma eggs with latex beads coated only with purified schistosoma soluble egg antigen (SEA). Culturing these beads with PBMC, T-cell clones or spleen cells in the absence of autologous serum proved to be the first practical in vitro models suited to study mechanisms regulating granuloma formation (Bentley et al., In vitro delayed hypersensitivity granuloma formation-development of an antigen-coated bead model", J Immunol, 1985; 134:4163-4169). The method of quantitating the immune contribution of cells in schistosomiasis-induced IVG's was according to the IVG size After 7 days in vitro, either PBMC and T-cells from patients or animals with active schistosomiasis showed enhanced cell adherence to the bead with larger IVG formation while cells from patients or animals not infected with schistosomiasis resulted in smaller IVG's. This model of chronic granulomatous inflammation was limited by dependency on the measurement of in vitro granuloma size to assess disease activity, e.g., differences between the most active and least active in vitro granulomas were often the adherence of only 1-2 cells per bead with over two million cells present. This lack of sensitivity and specificity of the in vitro granulomas in schistosomiasis limited this model's popularity.

Human granulomatous infections, such as sarcoidosis and Wegener's granulomatosis, have no known cause or cure. Granuloma formation in sarcoidosis is generally thought to result from T-cell and macrophage activation in response to a putative antigen, and has not been regarded as governed by circulating factors. Despite years of research, no such antigen has been discovered. No blood test for the presence of human granulomatous inflammation diseases currently exists. Present treatment has been confined to the use of dangerous immunosuppression drugs such as prednisone and cyclophosphamide.

SUMMARY OF INVENTION

A protein secreted by human cells, Granuloma Enhancing Factor (GEF), has been found to regulate human granulomatous inflammation. GEF can be measured in blood and body fluids such as lung lavage fluid or pleural fluid. The GEF assays of the present invention are useful to assist clinicians in diagnosing patients with granulomatous inflammation. Serum GEF activity has been found to be high in patients with active granulomatous inflammation with either unknown etiology, such as sarcoidosis, or known etiology, such as tuberculosis. Diseases such as sarcoidosis and Wegener's granulomatosis, which until this invention had no known cause or cure, may be both diagnosed and treated with the methods of the invention. It has been discovered that serum GEF activity, which is high in these diseases, can be blocked using a variety of methods including human immunoglobulin, blocking antibodies, and an inhibitor purified from human serum from patients recovered from granulomatous diseases. These interactions offer new therapeutic options.

In cases of infection due to fungi, mycobacteria or parasites where GEF activity should be elevated but is found to be low, for example in patients with immune deficient states such as the Acquired Immune Deficiency Syndrome (AIDS), the administration of GEF to regulate appropriate granulomatous responses is beneficial.

Further, the detection of different forms of GEF i.e., isoform or isoenzyme, allows a specific diagnosis to be made among the various granulomatous inflammatory diseases.

DESCRIPTION OF DRAWINGS

FIGS. 1a-1b is a graphical depiction showing the comparison between the subjective visual score and the objective video analysis of the IVG's which are used to determine the level of GEF in a bodily fluid for comparison with established diagnostic levels of GEF in accordance with the present invention IVG formation can be assessed either by computerized image analysis or by visual score. To compare the two methods, image analyses were performed on 10 beads in each of 3 wells for each visual score. Each bead (+) and the mean ± SEM (·) of all 30 beads for each score are shown.

DETAILED DESCRIPTION

The formation of induced in-vitro granuloma (IVG) using normal donor peripheral blood mononuclear cells (PBMC) with plain uncoated polyacrylamide beads and serum additions from patients with active granulomatous inflammation allowed the identification of the serum factor which has been designated Granuloma Enhancing Factor (GEF). Sera from patients with active sarcoidosis, active Wegener's granulomatosis or active mycobacterial disease were found to induce IVG's.

Granuloma formation in sarcoidosis is generally thought to result from T-cell and macrophage activation in response to a putative antigen, and has not been regarded as governed by circulating serum factors. The in vitro granuloma (IVG) model developed by Bentley et al. (1985) in which PBMC became adherent to polyacrylamide beads coated with Schistosoma mansoni soluble egg antigen was used. Since no soluble antigen has been elucidated in sarcoidosis, beads coated with tetanus toxoid, PPD or Kveim antigen were initially used. Spontaneous IVG's formed on all beads regardless of the antigen coating, in the absence of patient sera, using PBMC from sarcoidosis patients with active disease. The same phenomenon was observed with plain uncoated polyacrylamide beads, and it was concluded that no specific antigen addition in vitro was needed to activate antigen presenting cells in this spontaneous-IVG model (Mishra et al. "In-vitro sarcoid granulomas-differences between active and inactive disease". In: Grassi et al.: Sarcoidosis and Other Granulomatous Disorders, Amsterdam: Excerpta Medica; 1988, pp. 151-154). However, sera, pleural fluid and bronchoalveolar lavage fluid from patients with active sarcoidosis, active Wegener's granulomatosis or active mycobacterial disease either tuberculosis or atypical, induced IVG's using normal donor PBMC. The factor common to these granulomatous diseases has been designated Granuloma Enhancing Factor (GEF).

A method for the diagnosis of a human granulomatous inflammatory disease comprising determining the level of GEF activity in a bodily fluid and comparing said level to established diagnostic levels of said GEF is provided. As shown in Table 1, a healthy person should have a "subjective score" of 4 or less i.e., less than 20 peripheral blood mononuclear cells (PBMC) per bead. A person who develops a granulomatous disease such as tuberculosis or *Mycobacterium-avium intracellular* (MAI), should develop an elevated level of GEF as a desirable host response against the disease (i.e., >20 PBMC/bead), but if the diagnostic method of the invention indicates that they have not developed an elevated level of GEF despite the infection, then they can be treated by administering an effective amount of GEF either alone or in combination with a pharmaceutically acceptable carrier. Human purified GEF is the preferred GEF. Human granulomatous inflammatory diseases such as sarcoidosis, Wegener's granulomatosis, and Crohn's disease result from an elevated level of GEF, where the excessive GEF is not fighting an infectious disease agent but instead is causing a granulomatous disease itself. Such diseases can be treated in accordance with the present invention by blocking the inappropriately elevated GEF activity by administering a GEF-blocking agent in an effective amount. Useful blocking agents include human immunoglobulin, blocking antibodies such as an anti-GEF antibody or an antibody which blocks receptors on cells producing GEF and an inhibitor purified from human serum from patients recovered from granulomatous diseases

METHODS

Patients were diagnosed according to established clinical criteria. Blood, bronchoalveolar lavage fluid and pleural fluid were obtained. Neither patients nor normal donors had been treated with corticosteroid or immunosuppressive drugs within the previous three months.

Patients with sarcoidosis were classified as subacute (duration less than 2 years), chronic (greater than 2 years) or recovered (stable >2 years, no residuals of disease): subacute, active (SA); chronic, active (CA), chronic, inactive (CI) and recovered (R). Patients with Wegener's granulomatosis were classified on the basis of clinical and laboratory changes as active and inactive. Patients with mycobacterial infection had cultures positive for either *Mycobacterium tuberculosis* or *Mycobacterium-avium intracellular* (MAI) and were classified on the basis of clinical and laboratory changes as active or inactive.

Serum

Serum samples were drawn by standard venipuncture technique using Vacutainer TM Serum Separator Tubes (Becton-Dickinson). Serum samples were stored at $+4°$ C. until tested in the induced-IVG model and then at $-20°$ C. Serum and fluid filtrate/concentrates were obtained using Unisep-30 TM (Bio-Rad), Centricon-30 TM or Centricon-100 TM (Amicon) which allows separation of molecules of less than 30,000 MW or 100,000 MW by centrifugation.

Bronchoalveolar lavage (BAL) fluid

Bronchoalveolar fluid was obtained by standard clinical procedures and cells were separated from fluid not used for diagnostic purposes by centrifugation at 500 G × 10 minutes. BAL fluid was concentrated approximately 100 fold under nitrogen pressure using an Amicon 8050 stirred ultrafiltration cell equipped with a YM-30 Diaflo Ultrafilter ®.

Isolation of peripheral blood mononuclear cells from normal donor blood

Peripheral whole blood was collected in heparinized Vacutainer TM tubes (Becton-Dickinson) from one of five normal volunteers (selected by rotation for all experiments). The whole blood was diluted 2:1 with Hanks Balanced Salt Solution (HBSS). This mixture was underlayered with Ficoll-Paque TM (Pharmacia) at a 3:1 dilution and centrifuged at 525 G for 30 minutes at room temperature. The mononuclear cell layer (PBMC) was removed and washed 3 times in 50 ml HBSS (400 G × 10minutes). Cell viability, assessed using 0.05% trypan blue, exceeded 90% in all experiments. Cells were then suspended in complete medium (RPMI-1640 supplemented with 10% heat-inactivated fetal bovine serum, 2 mM L-glutamine, $0.5 \times 10^{-5}$ 2-mercaptoethanol, 20 mM Hepes buffer, 100 U/ml penicillin, 100 μg/ml streptomycin) at $0.5 \times 10^6$ cells/ml.

In-vitro granuloma (IVG)

PBMC were plated at $0.5 \times 10^6$ cells/ml of complete media per well in polystyrene flat bottom 24 well plates (Falcon Multiwell TM). Two hundred autoclave sterilized polyacrylamide beads (Biogel P-4 TM, 40-80μ, Bio-Rad) in 20-40 μl of sterile PBS were then added. A maximum of 0.1 ml of autologous control serum or 0.1 ml test serum was added to the wells. Plates were incubated at 37° C., in a 5% $CO_2$ humidified air atmosphere for the next seven days.

Granuloma image analysis

On day 1, 3, 5 and 7, both a subjective and objective assessment of granuloma size was made.

Subjective

A subjective visual assessment of the number of PBMC adherent to beads was performed using an inverted microscope (Nikon Diaphot TM) by scoring 5 beads as follows: 0-1 cells = subjective score of "1"; 2-5 cells = 2; 6-12 cells = 3; 13-20 cells = 4; greater than 20 cells = 5; complete circumferential monolayer cells = 6 and multiple layer cells equal a subjective score of 7 (FIG. 1 and Table 1).

Photos were taken with a mounted Nikon FE camera using Kodak Ektachrome 160 ASA or Kodak Tmax 3200 black and white film.

Objective

Visual counts and video recordings of 10 beads per well were made with a Wild inverted M40 microscope coupled to a Dage MTI-65 video camera and video recorder. Following image acquisition, image analysis of the recorded bead with adherent cells was performed by drawing circumferential outlines of each granuloma on a computer screen coupled to the Bioquant Image Analysis System. First the outer edge of the adherent cells was outlined to provide the total cell plus bead area. Next, the bead was outlined and the area of the bead was subtracted to provide the granuloma area in square μm (FIG. 1 and Table 1).

TABLE 1

| IN VITRO GRANULOMA (IVG) ANALYSIS | | |
|---|---|---|
| Cells Attached per bead | Subjective Score | Objective Area. $\mu m^2$ |
| 0-1 cells | 1 | 1,000 |
| 2-5 cells | 2 | 4,000 |
| 6-12 cells | 3 | 6,000 |
| 12-20 cells | 4 | 8,000 |
| >20 cells | 5 | 10,000 |
| Complete circumferential monolayer | 6 | 15,000 |
| Multiple layers | 7 | >20,000 |

Immunohistochemical staining of induced-IVG's

After 7 days incubation at 37° C. in a humidified 5% $CO_2$ atmosphere, the medium was carefully removed by capillary action of blotting paper strips so that the induced-IVG's were minimally disturbed. The wells were then fixed with methanol, washed with PBS, blocked with horse serum, and stained with the following antibodies:

anti-Leu-M5 (monocyte)
anti-Leu-2a (CD8)
anti-Leu-3a and 3b (CD4)
anti-Leu-14 (B cell)

All antibodies were obtained from Becton Dickinson, Mountain View, CA. Alkaline phosphatase substrate with levamisole was used for detection (Vectastain TM, Vector Laboratories, Burlingame CA). Photographs were taken with a mounted Nikon FE camera using Ektachrome 160 ASA or Kodak Tmax 3200 ASA black and white film. Control stains were mouse immunoglobulin $IgG_1$ and $IgG_{2a}$.

Additives

Cycloheximide and human IgG Sandoglobulin TM (Sandoz) were diluted using sterile PBS and added to the wells at the time of PBMC plating for in-vitro granulomas formation.

Serum assays

Angiotensin converting enzyme (ACE) activity was determined at 1:8 dilution using a modified FAPGG substrate (Maguire, G.A., et al, "A continuous monitoring spectrophotometric method for the measurement of angiotensin converting enzyme in human serum", *Ann Clin Biochem*, 1985; 22:204-210). The change in substrate absorbance was read at 320 nm using a Spectronic 1001 TM (Milton Roy) spectrophotometer equipped with an automatic sampler and flow cell.

Antinuclear cytoplasmic antibody (ANCA) was determined by both an ELISA and immunofluorescent technique. IgM-rheumatoid factor was determined using a standard latex particle assay. Immune complexes were determined by both Raji cell equivalent (Ciq binding) and circulating immune complex assays using immobilized monoclonal antibodies to C3 (Cytotech Co.).

Statistical analysis

Data with normal distribution were analyzed by Student's t-test; non-parametric data, such as the granuloma areas, were analyzed by the Kruskal-Wallis rank test. All statistical tests were performed using SYSTAT on an IBM AT computer. $P < 0.05$ was considered significant.

Results

FIG. 1 shows the comparison between the subjective visual score and the objective video analyses Comparing the visual score (subjective) with the video-image analysis (objective) of the induced-IVG disclosed a significant correlation when 10 beads were analyzed. Bead size, ranging from approximately 40-80 $\mu$m in diameter, was subtracted from the area of the induced-IVG by the image analysis system. As shown in Table 1, small IVG's (visual score 1-3) measured 1000-6000 $\mu m^2$; medium IVG's (visual score 4,5) measured 8000-10000 $\mu m^2$; large IVG's (visual score 6,7) measured $> 15000 \mu m^2$.

This induced-IVG model correctly identified 72% of active sarcoidosis patients and 70% of active Wegener's granulomatosis patients using comparison with control autologous serum. Inactive sarcoid and Wegener's patients were positive in 7 of 12 (58%) and 0 of 2 (0%), respectively. Seventy-five percent of the patients with pulmonary mycobacterial disease were positive. Only 19% of normal donors (controls) tested positive. There was no correlation with serum angiotensin converting enzyme (ACE) activity, antineutrophil cytoplasmic antibody titer (ANCA), rheumatoid factor (RF) and immune complexes.

Our induced-IVG model uses normal donor PBMC with uncoated polyacrylamide beads in a configuration similar to our previous model of the spontaneous IVG. In the presence of both 10% FCS and 10% autologous serum, only small induced-IVG's consisting cf 4-6 cells are formed on the beads. However, in the presence of 10% FCS and 10% serum from patients with active granulomatous disease, there zealous IVG induction with greater than 20 cells in multiple layers adherent to the bead.

The addition of cycloheximide in conjunction with serum containing GEF resulted in a disassembly of the large granuloma by day 3 indicating that protein synthesis by the cells forming the granuloma is a requirement. The addition of human immunoglobulin also had an inhibitory effect on IVG formation. Serum from patients recovered from granulomatous diseases also had an inhibitory effect on IVG formation.

The results of testing sera from patients with granulomatous inflammation are shown in Table 2.

TABLE 2

PRESENCE OF SERUM GRANULOMA ENHANCING FACTOR (VISUAL SCORE >4)*

| Sarcoidosis | | |
|---|---|---|
| Subacute active | 21/29 | 72% |
| Chronic active | 17/27 | 63% |
| Chronic inactive | 7/12 | 58% |
| Recovered | 1/6 | 16% |
| Wegener's granulomatosis | | |
| Active | 7/10 | 70% |
| Inactive | 0/2 | 0% |
| Mycobacterial infection | | |
| Tuberculosis, active | 7/10 | 70% |
| M.A.I., active | 8/12 | 75% |
| Normal Volunteers | 10/53 | 19% |
| Rheumatoid arthritis | 1/25 | 4% |

*Normal ≦4

Sera from patients having active sarcoidosis or Wegener's granulomatosis had the highest incidence of GEF. As disease activity was reduced, the incidence of GEF followed in a parallel fashion.

There was no correlation between GEF and serum angiotensin converting enzyme in sarcoidosis or between GEF and serum antineutrophil cytoplasmic antibody in Wegener's. For all groups of patients, there was no correlation between the presence of GEF and serum rheumatoid factor or the presence of immune complexes, indicating that GEF is a unique factor.

Immunohistochemical staining of IVG's

GEF Characterization

Analysis of filtrate and retentate fractions from ultracentrifugation disclosed GEF has a molecular weight greater than 100,000 daltons. GEF was heat stable at 56° C. for 30 minutes indicating it is not part of or dependent on the complement cascade.

CD4 positive lymphocytes were detected with M5 positive macrophages within the IVG; CD8 positive lymphocytes were noted on the periphery of the IVG. These findings support the immunologic (hypersensitivity) nature of the IVG's.

The shortcomings of this IVG model for studying human granulomatous inflammation are the dependency on normal donor PBMC and lengthy (labor intensive) granuloma size measurements, consistent with any bioassay procedure.

Scanning each well under an inverted microscope and then performing computer assisted measurements of IVG's at day 1, 3, 5 and 7 proved extremely time consuming. Since the IVG measurements in square micrometers correlate well with the subjective visual score, the rapidly assessed visual score allows rapid scanning of wells to derive IVG data without complete video analyses.

The induced-IVG model identifying Granuloma Enhancing Factor (GEF) in human body fluids appears to be ideally suited for studying hitherto neglected influences on granulomatous inflammation.

What is claimed:

1. A method for the diagnosis of a human granulomatous inflammatory disease comprising determining the level of Granuloma Enhancing Factor (GEF) activity in a bodily fluid and comparing said level to established diagnostic levels of said GEF.

2. A method for treating a human granulomatous inflammatory disease in a patient with a deficient level of Granuloma Enhancing Factor (GEF) activity comprising administering an effective amount of GEF either alone or in combination with a pharmaceutically acceptable carrier.

3. The method of claim 2 wherein said GEF comprises human purified GEF.

4. A method for treating a human granulomatous inflammatory disease resulting from an elevated level of Granuloma Enhancing Factor (GEF) activity comprising blocking GEF activity by administering a GEF-blocking agent in an effective amount.

5. The method of claim 4 wherein said GEF-blocking agent is human immunoglobulin.

6. The method of claim 4 wherein said GEF-blocking agent is a blocking antibody.

7. The method of claim 6 wherein said blocking antibody comprises an anti-GEF antibody or an antibody which blocks receptors on cells producing GEF.

8. The method of claim 4 wherein said GEF blocking agent is an inhibitor purified from human serum from patients recovered from granulomatous inflammation.

* * * * *